United States Patent [19]

Schmolka

[11] 4,376,764

[45] Mar. 15, 1983

[54] SILVER ION GEL COMPOSITIONS

[75] Inventor: Irving R. Schmolka, Grosse Ile, Mich.

[73] Assignee: BASF Wyandotte Corporation, Wyandotte, Mich.

[21] Appl. No.: 291,320

[22] Filed: Aug. 10, 1981

[51] Int. Cl.³ .................. A61K 31/74; A61K 31/625; A61K 33/38

[52] U.S. Cl. ........................................ 424/78; 424/132; 424/229; 424/290; 424/342; 424/DIG. 13

[58] Field of Search ................. 424/78, 132, 290, 342, 424/DIG. 13, 229; 568/624

[56] References Cited

U.S. PATENT DOCUMENTS 2,828,345  3/1958  Spriggs ................................ 260/216
3,057,890  10/1962  De Groote ..................... 568/624 X
3,639,575  2/1972  Schmocka .............................. 426/78
4,326,977  4/1982  Schmocka ........................... 252/106

FOREIGN PATENT DOCUMENTS 722746  1/1955  United Kingdom .

OTHER PUBLICATIONS

Block and Graft Copolymerization, vol. 2, R. J. Ceresa, Ed., 1976, pp. 68 and 69.

*Primary Examiner*—Leonard Schenkman
*Attorney, Agent, or Firm*—Bernhard R. Swick

[57] ABSTRACT

Silver ion gel compositions containing a polyoxybutylene-polyoxyethylene block copolymer that maintain their gel characteristics at temperatures below 20° C. These gel compositions may be used to treat burn wounds and superficial ulcers.

8 Claims, No Drawings

SILVER ION GEL COMPOSITIONS

BACKGROUND OF THE INVENTION

1. Field of the Invention

The invention relates to a silver ion gel composition comprising an amount of a silver salt effective to treat a burn wound, from about 65 to about 85 percent by weight of water and from about 15 to about 35 percent by weight of a polyoxybutylene-polyoxyethylene block copolymer. These aqueous gels maintain their gel characteristics at refrigerator and freezer temperatures and at ambient temperature or room temperature below 20° C. and are thus able to be stored at ambient temperature or room temperature without turning liquid.

2. Description of the Prior Art

U.S. Pat. No. 3,639,575 relates to silver ion gel compositions containing polyoxyethylene-polyoxypropylene block copolymers wherein the hydrophobe has a molecular weight of at least 2250 and a hydrophile portion constitutes from about 10 to 90 weight percent ethylene oxide based on the weight of the copolymer. These gels are prepared by dissolving the copolymer in water at a temperature between 1° C. and 10° C., adding the silver salt slowly to the cool copolymer solution, adding optional additives and allowing the solution to warm to room temperature whereby a clear ringing gel is formed.

Among the problems associated with the prior art gel compositions have been their liquid nature at refrigerator or freezer temperatures. The present invention is directed to the preparation of silver ion gel compositions devoid of these problems.

SUMMARY OF THE INVENTION

The invention relates to a silver ion gel composition comprising an amount of a silver salt effective to treat a burn wound, from about 65 percent by weight to about 85 percent by weight water and from about 15 percent by weight to about 35 percent by weight of a polyoxybutylene-polyoxyethylene block copolymer, said block copolymer being a cogeneric mixture of conjugated polyoxybutylene-polyoxyethylene compounds containing in their structure oxybutylene groups, oxyethylene groups and an organic radical derived from an organic compound containing a plurality of reactive hydrogen atoms, preferably a water soluble organic compound containing a plurality of reactive hydrogen atoms and 2 to 12 carbon atoms. The compounds are characterized in that all the oxybutylene groups are present in polyoxybutylene chains that are attached to the organic radical at the site of a reactive hydrogen atom thereby principally constituting a polyoxybutylene polymer. The oxyethylene groups are attached to the polyoxybutylene polymer in polyoxyethylene chains. The average molecular weight of the polyoxybutylene polymers in the mixture is at least 1200, as determined by hydroxyl number and the oxyethylene groups present constitute about 50 to about 80 percent by weight of the compound, with the provisos that (a) when the hydrophobe molecular weight is about 1200, then the minimum polyoxyethylene content is about 60 percent by weight of the block copolymer and the minimum block copolymer content to form a gel is about 25 percent by weight of the aqueous gel composition;

(b) when the hydrophobe molecular weight is about 1800, then the minimum polyoxyethylene content is about 55 percent by weight of the block copolymer and the minimum block copolymer content to form a gel is about 20 percent by weight of the aqueous gel composition;

(c) when the hydrophobe molecular weight is about 2400, then the minimum polyoxyethylene content is about 50 percent by weight of the block copolymer and the minimum block copolymer content to form a gel is about 16 percent by weight of the aqueous gel composition;

(d) when the hydrophobe molecular weight is about 3000, then the minimum polyoxyethylene content is about 45 percent by weight of the block copolymer and the minimum block copolymer content to form a gel is about 16 percent by weight of the aqueous gel composition. These gel compositions may be used to treat burn wounds and superficial ulcers and maintain their gel characteristics at temperatures below about 20° C.

DESCRIPTION OF THE PREFERRED EMBODIMENTS

The block copolymer of use in the invention is a cogeneric mixture of conjugated polyoxybutylene polyoxyethylene compounds having as a hydrophobe, a polyoxybutylene polymer of at least 1200 molecular weight. The polyoxybutylene compounds are prepared by first condensing butylene oxide with an organic compound containing a plurality of reactive hydrogen atoms to prepare a polyoxybutylene polymer of at least 1200 molecular weight, and subsequently condensing ethylene oxide thereto. The compounds used in this invention conform to the following generic formula:

$$Y[(C_4H_8O)_n-E-H]_x \qquad (A)$$

wherein Y is the residue of a water soluble organic compound containing therein x active hydrogen atoms; n is an integer; x is an integer greater than 1; the values of n and x are such that the molecular weight of the compound, exclusive of E, is at least 1200, as determined by hydroxyl number; E is a polyoxyalkylene chain wherein the oxygen/carbon atom ratio is at least 0.5, and E constitutes 50 percent by weight to 80 percent by weight of the compound.

The polyoxybutylene polymer, which is an intermediate in the preparation of the compounds of use in this invention, has the following structure:

$$Y[(C_4H_8O)_nH]_x \qquad (B)$$

wherein Y, n and x are defined as in Formula A above.

The preferred compounds of use in this invention are prepared by condensing ethylene oxide in an amount between 50 and 80 percent by weight of the resultant compound, with the polyoxybutylene polymer. These compounds have the following formula $$Y[(C_4H_8O)_n(C_2H_4O)_mH]_x \qquad (C)$$

wherein Y, n and x are defined as in Formula A and m has a value such that the oxyethylene groups constitute 50 to 80 percent by weight of the compound.

When ethylene oxide is condensed with a polyoxybutylene glycol of at least 1200 molecular weight and derived from a butanediol initiator, the resulting compounds have the following structure:

$$HO(C_2H_4O)_m(C_4H_8O)_n(C_2H_4O)_{m'}H \qquad (D)$$

where n is defined as previously set forth; and $m'+m$ have a value such that the oxyethylene groups constitute 50 percent by weight to 80 percent by weight of the compound.

The hydrophilic portion of the polyoxyalkylene compounds may be supplied in whole or in part by other polyoxyalkylene chains in lieu of the polyoxyethylene chain set forth in Formula C. Any polyoxyalkylene chain may be used provided that the oxygen/carbon ratio contained therein is at least 0.5.

Examples of a water-soluble organic compound containing therein x active hydrogen atoms, the residue of which is Y, are the initiators, which may include water, diols such as propanediol, butanediol, triols such as glycerol, tetrols such as pentaerythritol as well as initiators containing more than four hydroxyl groups such as hexitol or sucrose. Also, amines and other low molecular weight water-soluble compounds having two or more active hydrogen atoms such as ethylene diamine or diethylene triamine may be used as the initiator. Preferably used is butanediol. More preferably used is 1,4-butanediol.

The butylene oxide used in making the hydrophobic polyoxybutylene polymer, which is an intermediate in the preparation of the compounds used in this invention, may be replaced with up to 10 percent by weight of propylene oxide or ethylene oxide when added as a mixture with the butylene oxide. Also, up to 10 percent by weight of propylene oxide or butylene oxide may be used to replace ethylene oxide, when added as a mixture with ethylene oxide, in preparing the block copolymers used in this invention. In lieu of butylene oxide, other 4 carbon cyclic ethers such as methyloxetane, tetrahydrofuran and isobutylene oxide may be used.

The block copolymers, conforming to structure D above of use in this invention, are those block copolymers which contain a polyoxybutylene hydrophobe average molecular weight of a minimum of 1200 and preferably 1600 or higher, including 2000, 2400 and 3000. The ethylene oxide content in the block copolymer is between about 50 percent by weight to about 80 percent by weight based on the weight of the block copolymer, preferably about 60 percent by weight. The block copolymer is used in an amount from about 15 percent by weight to about 35 percent by weight of the silver ion gel composition.

The silver salts which are employed in the preparation of the gels of the present invention include both water-soluble and water-insoluble silver salts which will effectively prevent the growth of pseudomonas aeruginosa and proteus mirabilis and do not act as co-sensitizers where other heavy metal ions do. Representative silver salts are silver nitrate, silver acetate, silver sulfate, silver sulphadiazine, silver lactate and silver lactate monohydrate. The silver salts are used in an effective amount to treat a burn wound, preferably 0.1 percent by weight to 5.0 percent by weight.

In addition to the silver salts mentioned above, the compositions of the present invention may contain other nontoxic medicaments and additives commonly employed in the treatment of skin. Illustrative of these medicaments and additives are antibiotics such as Bacitracin, Neomycin sulfate; hormones such as cortisone and hydrocortisone; propylene glycol or other humectants; vitamins, lanolin, glycerine and various other oils.

The gel compositions of the invention are prepared by adding the molten polyoxybutylene-polyoxyethylene block copolymer slowly to the water at 50° C. and mixing slowly while maintaining the system at 40° C. to 50° C. When a clear solution is obtained, the water-soluble or water-insoluble silver salt is added, mixed for a minute or two, and the homogeneous solution transferred to a brown glass jar. The composition forms a gel while cooling down. It remains as a gel even when placed in the refrigerator.

As used herein, the term "gel" is defined as a solid or semi-solid colloid containing considerable quantities of water. The particles in the gel are linked in a coherent network which immobilizes the water. A colloidal solution of water as a dispersion medium is often called a hydrosol. The gels within the scope of the present invention are more specifically ringing gels and may be described as gels that have a firm jelly-like consistency; that is, by tapping the gel lightly, it will vibrate and return to its original configuration.

Not all of the block copolymers of Formula D above may be employed in the present invention. Because of the nature of aqueous solutions of these block copolymers, three variables affect the fomation of gels. These variables are the weight percent concentration of block copolymers in the gel, the molecular weight of the hydrophobe $(C_4H_8O)_n$ and the weight percent of the hydrophile portion $(C_2H_4O)_m + (C_2H_4O)_{m'}$ of the copolymer. These minima define a minimum weight percent concentration of the block copolymer with a specific molecular weight polyoxybutylene hydrophobe having a minimum weight percent of ethylene oxide condensed thereto that is necessary to form a gel. Thus at the minimum concentration with a specific molecular weight hydrophobe, a minimum weight percent of ethylene oxide is required before a specific block copolymer will form a gel in an aqueous solution.

The illustrative block copolymers of formula D above may be employed in the preparation of the gel dentifrice composition of the present invention are presented in Table I.

The minimum weight percent concentrations with specific molecular weight hydrophobes are set out in Table II.

TABLE I

| Block Copolymer | Molecular Weight of Hydrophobe (Avg.) | Weight Percent of Hydrophile (Avg.) | Approximate Total Molecular Weight of Copolymer | |
|---|---|---|---|---|
| | | | T | F |
| A | 1800 | 60 | 4500 | 4200 |
| B | 1900 | 80 | 6000 | 5700 |
| C | 1800 | 80 | 9000 | 8130 |
| D | 1200 | 70 | 4000 | 3765 |
| E | 1200 | 80 | 6000 | 5160 |
| F | 2400 | 60 | 6000 | 5670 |
| G | 2400 | 70 | 8000 | 7800 |
| H | 2400 | 80 | 12,000 | 11,000 |
| I | 3000 | 60 | 7500 | 6165 |
| J | 3000 | 70 | 10,000 | 9000 |
| K | 3000 | 80 | 15,000 | 11,000 |
| L | 1200 | 60 | 3000 | 2922 |

TABLE II

| Molecular Weight of Hydrophobe | Minimum Percent by Weight of Block Copolymer to form Gel | Minimum Percent by Weight of Ethylene Oxide Required |
|---|---|---|
| 1200 | 25 | 60 |
| 1800 | 20 | 55 |
| 2400 | 16 | 50 |

TABLE II-continued

| Molecular Weight of Hydrophobe | Minimum Percent by Weight of Block Copolymer to form Gel | Minimum Percent by Weight of Ethylene Oxide Required |
|---|---|---|
| 3000 | 16 | 45 |

The technical explanation for the formation of the gels of the invention is not entirely understood, and the explanation hereinafter is not to be considered as being limitative of the invention. However, the behavior of these block copolymers in forming the gels is believed to be explained on the basis of hydrate formation. It may be speculated that the hydrophobe may, in its own right, immobilize the water independently of the oxyethylene chain by hydrogen bonding. It should be noted that the preferred block copolymers used in the gels of this invention exhibit a hydrophobe lying between two equal hydrophiles. This structure suggests a loose micellar structure is obtained with this class of nonionics and that gel formation would readily involve entrapment of free water in addition to water due to hydrogen bonding.

The following examples will further illustrate the various aspects of the invention. Where not otherwise specified throughout the specification and claims, temperatures are in degrees centigrade, and parts, percentages and proportions are by weight.

EXAMPLE 1

A silver ion gel composition was prepared by adding molten Block Copolymer A slowly to water at 50° C. and mixing slowly while maintaining the system at 40° to 50° C. When a clear solution was obtained, the silver compound was added and the homogeneous solution transferred to a brown glass jar. The composition formed a gel while cooling down. The compounds and the parts by weight of the gels of Examples 1–5 are listed below in Table III.

TABLE III

| Component | 1 pbw | 2 pbw | 3 pbw | 4 pbw | 5 pbw |
|---|---|---|---|---|---|
| Block Copolymer A | 22.0 | 22.0 | 22.0 | 22.0 | 22.0 |
| Silver Nitrate | 0.5 | — | — | — | — |
| Silver Sulfadiazine | — | 0.5 | — | — | — |
| Silver Lactate Monohydrate | — | — | 0.5 | — | — |
| Silver Acetate | — | — | — | 0.5 | — |
| Silver Sulfate | — | — | — | — | 0.5 |
| Water | 77.5 | 77.5 | 77.5 | 77.5 | 77.5 |

The products of the invention form gels as they cool to room temperature and remain gels below about 20° C.

The embodiments of the invention in which an exclusive privilege or property is claimed are defined as follows:

1. A silver ion gel composition which remains a gel at temperatures below room temperature comprising an amount of water-soluble or water-insoluble silver salt effective to treat a burn wound, about 85 to about 65 percent by weight water and about 15 to about 35 percent by weight of a polyoxybutylene-polyoxyethylene block copolymer, said block copolymer being a cogeneric mixture of conjugated polyoxybutylene-polyoxyethylene compounds containing in their structure oxybutylene groups, oxyethylene groups and an organic radical derived from a water-soluble organic compound containing a plurality of reactive hydrogen atoms and 2 to 12 carbon atoms; the compounds being characterized in that all of the oxybutylene groups are present in polyoxybutylene chains that are attached to the organic radical at the site of a reactive hydrogen atom thereby constituting a polyoxybutylene polymer; the oxyethylene groups being attached to the oxybutylene polymer in polyoxyethylene chains; the average molecular weight of the polyoxybutylene polymers in the mixture being at least 1200, as determined by hydroxyl number, and the oxyethylene groups present constituting 50 to 80 percent, by weight, of the mixture, with the provisos that (a) when the oxybutylene polymer molecular weight is about 1200, then the minimum polyoxyethylene content is about 60 percent by weight of the block copolymer and the minimum block copolymer content to form a gel is about 25 percent by weight of the aqueous gel composition;

(b) when the oxybutylene polymer molecular weight is about 1800, then the minimum polyoxyethylene content is about 55 percent by weight of the block copolymer and the minimum block copolymer content to form a gel is about 20 percent by weight of the aqueous gel compositions;

(c) when the oxybutylene polymer molecular weight is about 2400, then the minimum polyoxyethylene content is about 50 percent by weight of the block copolymer and the minimum block copolymer content to form a gel is about 16 percent by weight of the aqueous gel composition;

(d) when the oxybutylene polymer molecular weight is about 3000, then the minimum polyoxyethylene content is about 45 percent by weight of the block copolymer and the minimum block copolymer content to form a gel is about 16 percent by weight of the aqueous gel composition.

2. The silver ion gel composition of claim 1 wherein the silver salt is water soluble.

3. The silver ion gel composition of claim 1 wherein the silver salt is water insoluble.

4. The gel composition of claim 2 wherein the silver salt is silver nitrate.

5. The gel composition of claim 3 wherein the silver salt is silver sulfadiazine.

6. The gel composition of claim 1 wherein the block copolymer has an average molecular weight of the polyoxybutylene polymer of about 1800 and the oxyethylene groups constitute about 60 percent by weight of the mixture.

7. The gel composition of claim 4 wherein the block copolymer has an average molecular weight of the polyoxybutylene polymer of about 1800 and the oxyethylene groups constitute about 60 percent by weight of the mixture.

8. The gel composition of claim 5 wherein the block copolymer has an average molecular weight of the polyoxybutylene polymer of about 1800 and the oxyethylene groups constitute about 60 percent by weight of the mixture.

* * * * *